(12) United States Patent
Herding et al.

(10) Patent No.: US 7,485,228 B2
(45) Date of Patent: Feb. 3, 2009

(54) REACTOR AND METHOD FOR ANAEROBIC WASTEWATER TREATMENT

(75) Inventors: Walter Herding, Hahnback (DE); Urs Herding, Ursensollen (DE); Kurt Palz, Crailsheim (DE); Rainer Thurauf, Amberg (DE); Stephan Prechtl, Amberg (DE); Rainer Scholz, Amberg (DE); Ralf Schneider, Lauf a. d. Pegnitz (DE); Johann Winter, Fensterbach-Wolfring (DE); Rolf Jung, Gunzenhausen (DE)

(73) Assignees: Atz-Evns, Sulzbach-Rosenberg (DE); Herding GmbH, Amberg (DE)

( * ) Notice: Subject to any disclaimer, the term of this patent is extended or adjusted under 35 U.S.C. 154(b) by 0 days.

(21) Appl. No.: 10/577,745

(22) PCT Filed: Oct. 29, 2004

(86) PCT No.: PCT/EP2004/012299
§ 371 (c)(1),
(2), (4) Date: Apr. 9, 2007

(87) PCT Pub. No.: WO2005/042418
PCT Pub. Date: May 12, 2005

(65) Prior Publication Data
US 2007/0251880 A1  Nov. 1, 2007

(30) Foreign Application Priority Data
Oct. 29, 2003  (DE) .............................. 103 50 502

(51) Int. Cl.
*C02F 3/28*  (2006.01)
(52) U.S. Cl. ...................... 210/603; 210/615; 210/617; 210/194
(58) Field of Classification Search ............... 210/603, 210/615, 605, 630, 150, 194, 616, 617, 130, 210/196
See application file for complete search history.

(56) References Cited

U.S. PATENT DOCUMENTS 4,561,974 A  12/1985  Bernard et al. .............. 210/151

(Continued)

FOREIGN PATENT DOCUMENTS

DE  200 21 046 U1  3/2001

(Continued)

OTHER PUBLICATIONS

I. Morvai et al. "*Application of UASB-Reactors to Industrial Wastewater Treatment; Performance Data and Results in Granulation Control*"; Acta Biotechnol. 11(1991) 5. pp. 409-416.

(Continued)

*Primary Examiner*—Fred Prince
(74) *Attorney, Agent, or Firm*—Dorsey & Whitney LLP

(57) ABSTRACT

A reactor (10) for anaerobic waste water treatment is designed as a loop-type column reactor comprising a central flow channel (20). In the annular space (40) between the central flow channel (20) and the reactor wall, there are positioned carrier elements (50) for immobilizing microorganisms, with flow passages being provided between adjacent carrier elements (50). The lower portion of the reactor (30), below the carrier elements, is designed as a space intended to receive waste water having microorganisms floating therein during operation of the reactor (10). During operation, there are provided both floating microorganisms and microorganisms that are immobilized on the carrier elements. The waste water to be treated flows centrally downward and up again along the carrier elements (40), with the flow being generated in part by the gas development of the microorganisms. The reactor is used to carry out a process for anaerobic waste water treatment, the reactor being suited for waste water treatment in the food processing industry and the feeding stuff industry as well as in the paper industry and the textile industry.

64 Claims, 2 Drawing Sheets

U.S. PATENT DOCUMENTS

| | | | |
|---|---|---|---|
| 4,618,418 A | 10/1986 | Heijnen et al. | 210/151 |
| 4,632,692 A * | 12/1986 | Lebesgue et al. | 71/10 |
| 5,441,634 A * | 8/1995 | Edwards | 210/194 |
| 5,616,240 A * | 4/1997 | Sonnenrein | 210/104 |
| 5,618,412 A | 4/1997 | Herding et al. | 210/150 |
| 6,811,701 B2 * | 11/2004 | Wilkie | 210/603 |
| 2002/0162795 A1 * | 11/2002 | Pollock | 210/621 |
| 2007/0251880 A1 * | 11/2007 | Herding et al. | 210/603 |

FOREIGN PATENT DOCUMENTS

| | | | |
|---|---|---|---|
| EP | 0 303 149 A2 | 2/1989 | |
| JP | 60 232295 | 11/1985 | |
| JP | 61 174995 | 8/1986 | |
| JP | 03 178394 | 8/1991 | |
| JP | 5-50089 | 3/1993 | |

OTHER PUBLICATIONS

J. W. Morgan et al. "*Upflow Sludge Blanket Reactors: The Effect of Bio-supplements on Performance and Granulation*", International Journal of Biotechnical and Chemical Processes, 1991, 52, pp. 243-255.

\* cited by examiner

REACTOR AND METHOD FOR ANAEROBIC WASTEWATER TREATMENT

The present invention relates to a reactor and a process for anaerobic waste water treatment.

For the treatment of organically contaminated waste water, it is known to employ anaerobic processes and waste water treatment systems, respectively, operating in anaerobic manner. The contaminant load contained in the waste water, upon utilization of anaerobic technology, is transferred with the aid of corresponding microorganisms into the regenerative energy carrier biogas permitting savings in the energy purchased. The processes used therefor comprise both simple processes without biomass enrichment as well as high-performance processes using as a rule an internal biomass enrichment.

Municipal waste water contains comparatively low contaminant loads with a chemical oxygen demand (COD) of approx. 500 mg/l and as a rule is treated with aerobic activated sludge processes. In the food processing industry, there is waste water with considerably higher organic contaminant loads having a COD of more than 1,000 and up to 100,000 mg/l and more. For cleaning such waste water, there are employed high-performance processes.

The most common process is the so-called UASB process (upflow anaerobic sludge blanket process). In UASB reactors, there is effected an internal biomass enrichment in the form of a sludge which forms and has very good granulating properties. The microorganisms aggregate to form so-called pellets. These are aggregations having a size of approx. 1 to 3 mm. The reactors are operated in upflow-fashion, i.e. the waste water flows from below in upward direction through the reactor. Due to the metabolically effected degradation of the organic contaminants, there are formed gasses adhering to the pellets in the form of gas bubbles. Consequently, the pellets rise upwardly, causing thorough mixing in the system. In the upper portion of the UASB reactor, there is provided a separator system serving to retain the pellets in the reactor. An advantage of these reactors consists in that they may have a relatively simple construction, e.g. in the form of a loop-type column reactor. Such a reactor is described in DE 43 33 176. A disadvantage of this technology consists in that, with high COD concentrations starting from about 20 to 30 g/l, the gas development becomes so strong that the pellets rise upwardly very fast and that, in spite of the separator systems, there is a considerable loss of biomass taking place. This is referred to as "wash-out effect". Furthermore, there is the fact that these systems are relatively sensitive to poisoning (sensitive against a so-called toxic impact). Although these systems may be relatively quickly restarted after failure of the reactor, by inoculating using new biomass, this represents a cost factor. Another disadvantage of this process consists in that only such microorganisms may be used that form pellets, which greatly limits the choice of microorganisms. As a rule, there are employed methane-producing bacteria mainly of the class *Methanotrix*.

Another high-performance process makes use of fixed-bed reactors, in which inert carrier materials in the form of bulk material, packages or also fixed carrier materials, e.g. in the form of plate-like carrier elements, are populated with microorganisms. Such a reactor is described in the patent DE 43 09 779 of the same applicant. Fixed-bed reactors are suitable for treating very heavily contaminated waste water with COD concentrations of above 80 g/l. A disadvantage of the fixed-bed reactor is that the costs are high in particular when high-performance carrier materials are employed.

In addition thereto, there are also known fluidized-bed reactors in which the biomass is immobilized in a fluidized fixed bed, e.g. activated carbon or sand, which is swirled in the reactor. This necessitates a high demand of energy for maintaining the fluidized bed, which at the same time results in high loads being imposed on the reactor. The construction of fluidized-bed reactors accordingly is technically complex and sophisticated.

It is the object of the invention to make available a reactor and a process for anaerobic waste water treatment which is suited for waste water with high contaminant loads and operates with little trouble and is comparatively inexpensive.

This object is met by a reactor for anaerobic waste water treatment, comprising the following features:

(a) a central flow channel extending from the top in downward direction and terminating at the top with a first distance from the upper reactor confines and terminating at the bottom with a second distance from the lower reactor confines;

(b) in the annular space between the central flow channel and the reactor wall, there are positioned, either for the entire height of the flow channel or for part of the height of the flow channel, carrier elements for immobilizing microorganisms in the form of a structured, ordered fixed bed, with flow passages being provided between adjacent carrier elements;

(c) a lower portion of the reactor, between the lower confines thereof and the carrier elements, is in the form of a space intended to receive waste water with microorganisms floating therein during operation of the reactor;

(d) an upper portion of the reactor between the upper confines thereof and the carrier elements;

(e) the reactor, with respect to the internal flow thereof, is in the form of a loop-type column reactor such that waste water contained therein can be circulated through the central flow channel in downward direction, then through said space in the lower portion, then along the carrier elements in upward direction and finally again into the central flow channel;

(f) a supply line for waste water to be treated and to be introduced into the reactor for the first time;

(g) a discharge system for finally discharging treated waste water from the reactor.

The invention provides a hybrid reactor (and a hybrid process, respectively) which combines the advantages of fixed-bed reactors and UASB reactors.

The reactor may be of cylindrical shape, but other reactor geometries are possible as well, e.g. cylinder-like arrangements with elliptic or polygonal base or cuboidal arrangements.

The space in the lower portion is adapted to receive waste water having microorganism pellets floating therein. The microorganisms, due to the metabolism thereof, generate gasses adhering to the pellets in the form of bubbles and thus carrying the pellets upwardly. The microorganisms employed are preferably bacteria of the genus *Methanotrix*.

Preferably, there is arranged a separator system in the upper portion, which retains microorganisms floating in the waste water in the reactor.

Furthermore, the reactor preferably comprises a recirculation system having a withdrawal means for waste water and a supply means for waste water for flow delivery to the central flow channel.

The withdrawal means preferably has an intermediate space provided between two plate-shaped elements and a conduit starting in said intermediate space.

It is particularly preferred to arrange the discharge system for final discharge of treated waste water at a location somewhat above the withdrawal means of the recirculation system.

Microorganism pellets rising to the upper portion of the reactor are retained by the separator system, release the gas bubbles adhering thereto and sink downwardly again due to their higher density. The separator system may serve both for separating the gasses generated and for retaining the biomass.

The separator system preferably has a partition provided in spaced apart manner above the upper end of the central flow channel and covering a large part of the reactor cross-sectional area while leaving free an outer annular area.

The withdrawal means of the recirculation system preferably is positioned on the upper side of the partition. In the space above the withdrawal means of the recirculation system there is thus created a zone with reduced flow, enhancing the discharge of treated waste water without discharge of biomass, in particular as it is preferred—as mentioned hereinbefore—to arrange the discharge system for final discharge of treated waste water some distance above the withdrawal means of the recirculation system.

It is emphasized that the described recirculation system as well as the described separation of the withdrawal means of the recirculation system and the discharge system on the one hand constitute a preferred development of the invention disclosed, but on the other hand can be technically realized also without the features (or only with part of the features) of claim 1. A typical example is the realization in an UASB reactor which is not a hybrid reactor in the sense of the present application.

The partition of the separator system preferably has portions in which it is not extending horizontally and forms a gas collection space in a highest portion.

Furthermore, it is preferred that the partition—roughly speaking—extends outwardly from the highest portion in downwardly inclined direction and extends inwardly from the highest portion in downwardly inclined direction.

Preferably, a first discharge line for gas formed in the reactor starts in the upper portion of the reactor.

It is preferred furthermore that a second discharge line for gas formed in the reactor starts in the region of the partition.

The reactor has carrier elements provided therein. The carrier elements may be in the form of plates. The carrier elements preferably are arranged parallel to each other. The plates may be arranged in packages, with the plates within the packages being arranged in tangential direction of the reactor. The carrier elements are arranged above the space in the lower portion, so that the pellets floating upwardly pass between the plates. During operation of the reactor, microorganism growth is formed on the carrier elements. It is preferred to have a distance of 3 to 6 cm, preferably 3.5 to 5.5 cm, between the carrier elements.

The carrier elements may be made of inert material with a large surface. Preferably, they consist of a material that is porous to permit flow therethrough. In particularly preferred manner, the carrier elements consist substantially of plastics particles and expanded clay particles that are unified with each other. Polyethylene particles are preferred, with other plastics materials being possible as well. The microorganisms may deposit or seed in the pores of the expanded clay particles and in the pores between the particles and form a film-like or lawn-like growth on the carrier elements. In case of failure of the reactor, e.g. due to a toxic impact, the microorganism film is indeed destroyed. However, the microorganisms may rapidly re-grow from the pores of the porous carrier material and regenerate the film on the plates. The plates of the carrier elements may be populated or seeded with a large variety of microorganisms, e.g. bacteria. It is possible to seed the carrier elements at the same time with different species. The carrier elements may be seeded with the same species that forms freely floating aggregations or pellets. It is possible just as well to seed the carrier elements with other species than those forming the pellets. The advantages of the UASB process may thus be combined with the advantage of a larger variety of usable microorganisms.

The carrier elements can be seeded with sessile microorganisms. In particular, they may be seeded with the classes *Sytrophobacter, Sytrophomas, Methanotrix, Methanosarcina* and *Methanococcus.*

The inventors have found out that the synergetic effects (high performance with stable operation) of the combination of a fixed-bed reactor and an UASB reactor take place already with a relatively low percentage of carrier plates in relation to the reactor volume. It is thus preferred that the percentage of the reactor volume occupied by carrier plates be 15 to 40%. In particularly preferred manner, the percentage is 20 to 30%.

Preferably, the lower portion of the reactor has a flow deflection means positioned on the wall thereof. This flow deflection means has the function of separating the waste water stream from the reactor wall and of passing the same to the carrier elements in uniform manner.

Preferably, the reactor may have at least one driving jet outlet that terminates below the lower end of the central flow channel. This outlet serves for swirling microorganisms that have deposited on the reactor bottom. The outlet may have a nozzle at its end.

The object according to the invention furthermore is met by a process for anaerobic waste water treatment in a reactor in which waste water to be treated circulates, such that waste water (a) flows centrally from above to below;
(b) then is in contact with microorganisms floating in the waste water in a space in the lower portion of the reactor;
(c) then flows along microorganisms in a space of the reactor located thereabove, the microorganisms being arranged on carrier elements in the form of a structured, ordered fixed bed;
(d) and finally merges again into the central flow from above to below.

Upon flowing past the microorganisms on the carrier elements, part of the waste water preferably is branched off and pumped into the central flow channel. This improves the recirculation of the waste water in the cycle.

In the process according to the invention, the microorganisms floating in the treatment space preferably are in the form of pellets. The microorganisms floating in the waste water are retained by a separator system. The process may make use of different kinds of microorganisms as microorganisms immobilized on the carrier elements on the one hand and as floating microorganisms on the other hand. There may be provided different species of microorganisms on the carrier elements.

The reactor and the process according to the invention can be used for the treatment of waste water, in particular for the anaerobic treatment of waste water.

According to the invention, there is treated in particular organically contaminated waste water from the beverage industry, the feeding stuff industry or the food processing industry, e.g. waste water from starch processing factories and plants, beverage factories, breweries, spirits distilleries, dairies, waste water from meat and fish processing factories. The process according to the invention and the reactor according to the invention are suitable as well for treating waste water from the paper industry and the textile industry.

An embodiment of the invention will be explained in the following in exemplary manner by way of the drawings, in which FIG. 1 shows a schematic representation of an embodiment of the reactor for waste water treatment according to the invention;

An embodiment of the reactor according to the invention was constructed and utilized for the treatment of waste waster in a brewery.

Figure 1:
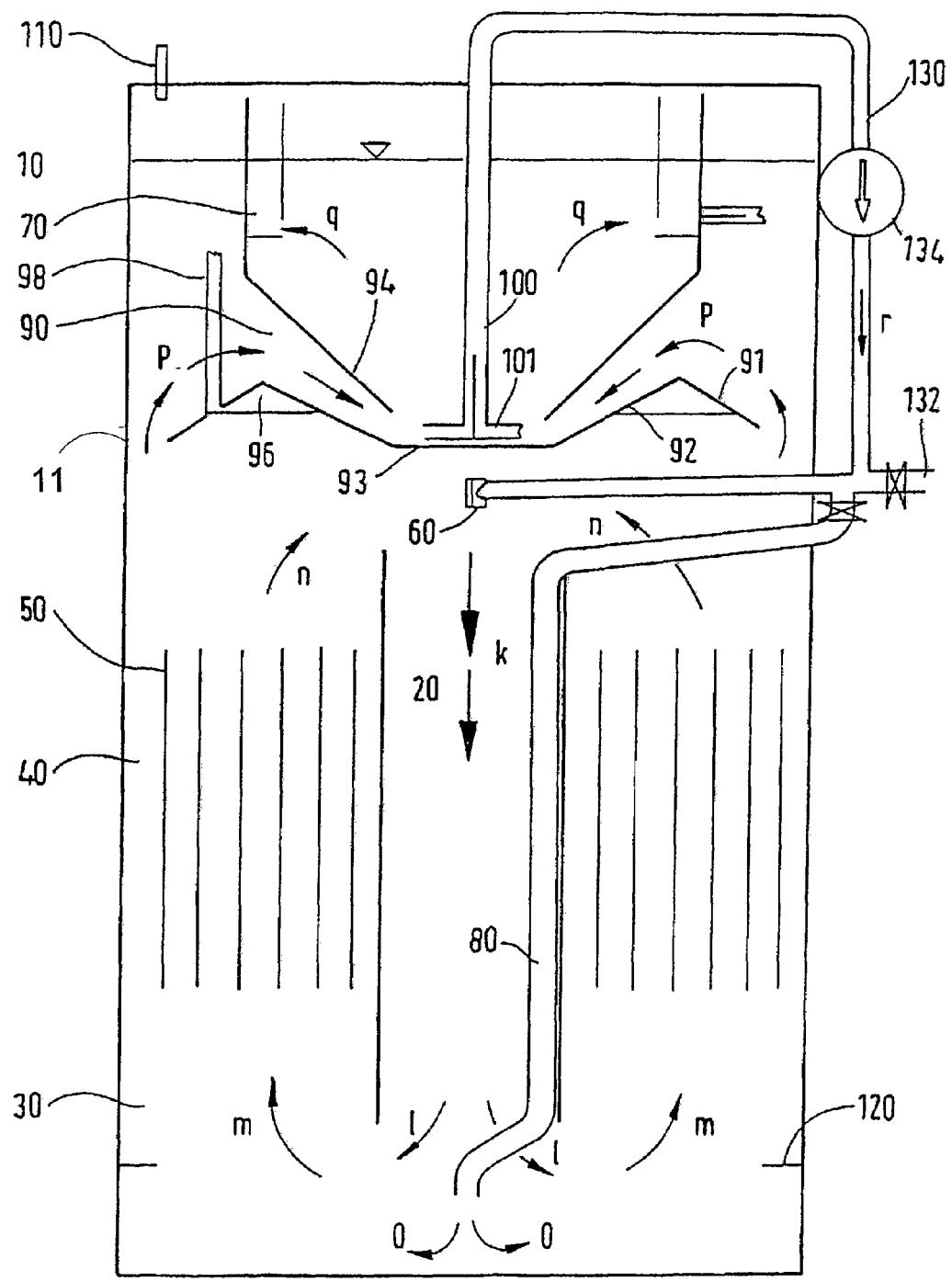

FIG. 1 shows the schematic construction of the reactor 10. The reactor is designed in the form of a loop-type column reactor. The dimensions of the cylindrical reactor are such that the height is between 2.0 and 5.0 m and the diameter is between 1.5 and 2.5 m. The quantity of waste water to be treated is between 10 and 20 m$^3$/d. The dimensions of the other reactor components can be seen in relation to the overall dimensions from FIG. 1. This reactor is designed for test operation. Technical designs for reactors in a large scale have clearly larger dimensions, e.g. a diameter of 5 to 9 m and a height of 8 to 12 m. Other reactor geometries are possible as well, e.g. cylinder-like arrangements with elliptic or polygonal base or cuboidal arrangements.

The reactor case 11 substantially consists of stainless steel sheets, as known from the prior art.

In the reactor 10, a central tube 20 is formed in axial direction, which starts in a distance from the upper end of the reactor and opens into the lower portion 30. The central tube 20 is of hexagonal shape in cross-section. This hexagonal shape is expedient in terms of manufacture, and packages with carrier elements 50 may be arranged in correspondence with the hexagonal shape. Other geometries are possible as well, e.g. circular or polygonal with a different number of corners. The lower portion 30 is in the form of a compartment or space in which the floating microorganisms are present during operation. Above the lower portion 30, there is provided a middle portion 40 having plate-shaped carrier elements 50 arranged in parallel therein, such that flow passages are present in vertical direction between these carrier elements. This arrangement of the carrier elements serves as fixed bed for seeding microorganisms.

The carrier elements are porous to permit flow therethrough and consist of a material formed substantially of unified plastics and expanded clay particles. Such a material is described in the afore-mentioned patent specification DE 43 09 779 of the same applicant.

The plates preferably are spaced apart by a distance of 3 to 6 cm, with a distance of 3.5 to 5.5 cm being particularly preferred. As seen in a plan view of the reactor cross-section, the carrier elements are arranged tangentially in packages constituting segments of a hexagon. Other arrangements are conceivable as well, e.g. arrangements of rectangular packages, of packages having the basic shape of a polygon or arrangements with curved plates.

To ensure sufficient biomass retention, the reactor is provided with a separator system 90 formed of inclined guide elements 91, 92, 93, 94. These guide elements prevent the discharge of solid particles, e.g. of pellets with gas bubbles. There are also other arrangements of the guide elements conceivable.

The guide elements 91, 92, 93, 94 may imitate the plan view of the hexagonal or polygonal fixed bed shape or may be of round design.

The flow path is illustrated by way of the arrows k, l, m, n, o, p, q and r. The waste water to be treated is supplied substantially via supply line 60, sucking in liquid from external space 40 and flowing through the central tube 20 into the lower portion 30 during operation, where floating microorganisms are present in the form of pellets. A partial stream optionally is supplied via tube 80, so as to provide for an additional mixing effect in the lower part of reactor 30. A flow hindrance 120 extending circumferentially along the inner reactor wall and being arranged in the lower portion 30 of the reactor serves for flow separation, so that the waste water to be treated cannot rise preferably along the container wall. The microorganisms used belong to the genus *Methanotrix*. Due to their metabolism, these bacteria produce gasses adhering to the pellets in the form of small bubbles. The pellets thus rise and generate additional flow movement of the waste water. In doing so, the waste water to be treated is flown past the microorganisms on the carrier elements and contacted with the same. At a partition formed of guide elements 91, 92, 93, the pellets are retained and release the gas bubbles due to the agitation created at the guide elements and may then drop again through the central tube 20 to the lower portion 30 because of their higher density as compared to the waste water. The partition forms a gas collection compartment or space 96 in which gas can be collected and discharged via a first gas discharge means 98.

This partition formed of the guide elements 91, 92, 93 covers a large part of the reactor cross-sectional area, leaving free an annular area between its outer edge and the reactor wall. Part of the flow along the carrier elements is branched off at the outer edge of the partition 91, 92, 93 and withdrawn from the upper portion above partition 91, 92, 93 and below guide elements 94 by way of a waste water withdrawal means 100, 101 and is recirculated again to the reactor via a recirculation system 130 comprising a pump 134.

The guide elements 94, in the upper portion of the reactor above the partition 91, 92, 93 and above the withdrawal means of the recirculation system, form a settlement zone from which treated waste water can be discharged from the reactor via a discharge system 70.

The gasses formed may be discharged via a second gas discharge line 110 at the upper end of the reactor.

Figure 2A:
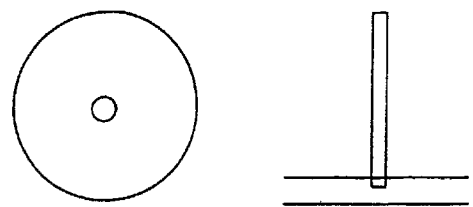
FIG. 2A shows a schematic representation of an embodiment of a withdrawal means for waste water of the reactor according to the invention.
Figure 2B:
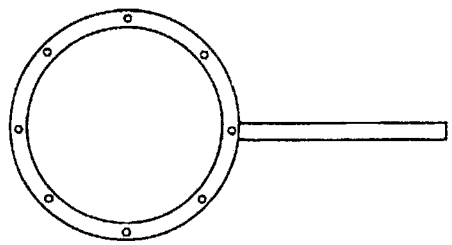
FIG. 2B shows a schematic representation of an alternative embodiment of a withdrawal means for waste water of the reactor according to the invention.
Figure 2C:
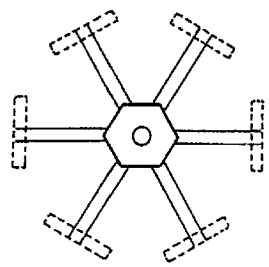
FIG. 2C shows a schematic representation of an additional alternative embodiment of a withdrawal means for waste water of the reactor according to the invention.

Preferred withdrawal means of the recirculation system are illustrated in FIGS. 2A, 2B and 2C.

FIG. 2A illustrates the so-called double-plate discharge means. It consists of two circular plates arranged on top of each other with a spacing of 40 to 70 mm therebetween, with the liquid being discharged centrally between said plates. This arrangement ensures discharge at low flow rates at the outer periphery of the plates.

FIG. 2B illustrates an annular conduit with holes. To ensure uniform liquid discharge, the holes are of different sizes, as shown in FIG. 2.

FIG. 2C illustrates are star-shaped tube discharge means allowing liquid to be discharged at six locations. When the tube ends are provided with T-pieces (shown in broken lines), the liquid may be discharged at 12 locations.

Figure 2D:
FIG. 2D shows a schematic representation of a discharge system of the reactor according to the invention.

FIG. 2D illustrates a discharge system having a submerged discharge channel with discharge holes. The hole size and the number of the holes are chosen to ensure uniform discharge of the treated waste water.

The required quantity of circulating water for the supply line shown at numeral 60 is provided via the recirculation system 130. Waster water to be supplied to the reactor for the first time can be introduced into the system via line 132. If necessary or in periodic intervals, part of the waste water introduced or circulating is passed via tube 80 to the lower portion of the reactor in the form of a driving jet in order to swirl the biomass (the microorganism pellets) present there. In larger reactors, there may be provided several driving jet outlets to obtain swirling of the biomass.

We claim:

1. A hybrid reactor for anaerobic waste water treatment, comprising:
   a plurality of porous carrier elements occupying at least part of the height of the hybrid reactor;
   a space in a lower portion of the hybrid reactor between the lower confines thereof and the carrier elements;
   an upper portion of the hybrid reactor between the upper confines thereof and the carrier elements;
   a supply line for waste water to be treated and to be introduced into the hybrid reactor for the first time;
   a discharge system for discharging treated waste water from the hybrid reactor,
   a central flow channel extending from the top of the hybrid reactor in downward direction from a first distance from the upper confines of the reactor to a second distance from the lower confines of the reactor;
   a space between the central flow channel and a wall of the hybrid reactor in which the carrier elements are positioned, the space extending for at least part of the height of the flow channel, the carrier elements forming a structured, ordered fixed bed to permit flow therethrough, the carrier elements being arranged with flow passages having a predetermined width range between adjacent carrier elements;
   a separator system located in the upper portion of the hybrid reactor below the discharge system, the separator system being structured to retain microorganisms floating in the waste water in the hybrid reactor and to separate water passed between the carrier elements into a first partial flow flowing into the central flow channel at the top end of the hybrid reactor, and a branched-off second partial flow;
   the hybrid reactor being structured to allow the waste water flow in the hybrid reactor in a loop through the central flow channel in downward direction, then through the space in the lower portion, then along the carrier elements in upward direction, and finally again into the central flow channel; and
   a recirculation system structured to withdraw water from the second partial flow and recirculate the withdrawn water into the waste water loop flow, the recirculation system including a withdrawal member positioned above a portion of the separator system and at a lower level than the discharge system.

2. The hybrid reactor of claim 1, wherein the carrier elements comprise plate-shaped carrier elements.

3. The hybrid reactor of claim 2, wherein a plurality of packages of the carrier elements are distributed across the circumference of the hybrid reactor, with the plate-shaped carrier elements within each package being arranged parallel to each other and in tangential direction of the hybrid reactor.

4. The hybrid reactor of claim 1, wherein the flow passages between adjacent carrier elements each have a width of 3 to 6 cm.

5. The hybrid reactor of claim 1, wherein the carrier elements comprise carrier elements substantially of plastics particles and expanded clay particles that are unified with each other.

6. The hybrid reactor of claim 1, wherein the withdrawal member of the recirculation system comprises an intermediate space between two plate-like elements as well as a conduit starting in the intermediate space.

7. The hybrid reactor of claim 1, wherein the separator system comprises a partition provided in spaced apart manner above the upper end of the central flow channel and covering a major part of the reactor cross-sectional area while leaving free an outer annular area.

8. The hybrid reactor of claim 7, wherein the partition comprises partition portions extending in a direction other than horizontally and forms a gas collection space in a highest portion.

9. The hybrid reactor of claim 8, wherein, from the highest portion, the partition extends outwardly in downwardly inclined manner and inwardly in downwardly inclined manner.

10. The hybrid reactor of claim 7, wherein the withdrawal member of the recirculation system is positioned at the upper side of the partition.

11. The hybrid reactor of claim 7, further comprising a second discharge line for gas formed in the hybrid reactor starts in the region of the partition.

12. The hybrid reactor of claim 1, further comprising a first discharge line for gas formed in the hybrid reactor and structured to remove gas in the upper portion of the hybrid reactor.

13. The hybrid reactor of claim 1, wherein the carrier plates are positioned in 15 to 40% of the reactor volume.

14. The hybrid reactor of claim 1, further comprising a flow hindrance positioned on the wall of the lower portion of the hybrid reactor.

15. The hybrid reactor of claim 1, further comprising at least one driving jet outlet terminating below the lower end of the central flow channel.

16. The hybrid reactor of claim 1, further comprising immobilized microorganisms and microorganism pellets, the microorganisms in the pellets being different from the immobilized microorganisms.

17. A process for anaerobic waste water treatment in a hybrid reactor combining using microorganism pellets and fixed-bed immobilization of microorganisms, in which the waste water to be treated circulates in the hybrid reactor, the process comprising:
   directing a mixture of the waste water and the microorganism pellets through a space in the lower portion of the hybrid reactor;
   then directing the mixture of the waste water and the microorganism pellets upwardly in a space of the hybrid reactor,
   immobilizing microorganisms in the mixture of the waste water and the microorganism pellets using a structured, ordered fixed bed on carrier elements that are porous to permit flow therethrough and form flow passages between each other;
   then directing the mixture of the waste water and the microorganism pellets to a separator system serving to retain microorganisms floating in the waste water in the hybrid reactor and separating the waste water into a first partial flow, and a second partial flow;
   directing the first partial flow centrally in the hybrid reactor from the top in a downward direction back into the space in the lower portion of the hybrid reactor; and recirculating at least part of the waste water in the second partial flow into the waste water flow in the hybrid reactor.

18. The process of claim 17, further comprising immobilizing microorganisms in the mixture of the waste water and the microorganism pellets.

19. A hybrid reactor for anaerobic waste water treatment, comprising:
a plurality of porous carrier elements occupying at least part of the height of the hybrid reactor;
a space in a lower portion of the hybrid reactor between the lower confines thereof and the carrier elements;
an upper portion of the hybrid reactor between the upper confines thereof and the carrier elements;
a supply line for waste water to be treated and to be introduced into the hybrid reactor for the first time;
a discharge system for discharging treated waste water from the hybrid reactor,
a central flow channel extending from the top of the hybrid reactor in downward direction from a first distance from the upper confines of the reactor to a second distance from the lower reactor;
the hybrid reactor being structured to allow the waste water flow in the hybrid reactor in a loop through the central flow channel in downward direction, then through the space in the lower portion, then along the carrier elements in upward direction, and finally again into the central flow channel;
a space between the central flow channel and a wall of the hybrid reactor in which the carrier elements are positioned, the space extending for at least part of the height of the flow channel, the carrier elements forming a structured, ordered fixed bed to permit flow therethrough, the carrier elements being arranged with flow passages each having a predetermined width range between adjacent carrier elements of 3 to 6 cm; and
a separator system located in the upper portion of the hybrid reactor below the discharge system, the separator system being structured to retain microorganisms floating in the waste water in the hybrid reactor.

20. The hybrid reactor of claim 19 wherein the carrier elements comprise plate-shaped carrier elements.

21. The hybrid reactor of claim 19 wherein the carrier elements comprise carrier elements substantially of plastics particles and expanded clay particles that are unified with each other.

22. The hybrid reactor of claim 19 wherein the separator system comprises a partition provided in spaced apart manner above the upper end of the central flow channel and covering a major part of the reactor cross-sectional area while leaving free an outer annular area.

23. The hybrid reactor of claim 19, further comprising a first discharge line for gas formed in the hybrid reactor and structured to remove the gas in the upper portion of the hybrid reactor.

24. The hybrid reactor of claim 19, further comprising a flow hindrance positioned on the wall of the lower portion of the hybrid reactor.

25. The hybrid reactor of claim 19, further comprising at least one driving jet outlet terminating below the lower end of the central flow channel.

26. The hybrid reactor of claim 19, further comprising immobilized microorganisms and microorganism pellets, the microorganisms in the pellets being different from the immobilized microorganisms.

27. A hybrid reactor for anaerobic waste water treatment, comprising:
a plurality of porous carrier elements occupying at least part of the height of the hybrid reactor, the carrier elements comprising carrier elements substantially of plastics particles and expanded clay particles that are unified with each other;
a space in a lower portion of the hybrid reactor between the lower confines thereof and the carrier elements;
an upper portion of the hybrid reactor between the upper confines thereof and the carrier elements;
a supply line for waste water to be treated and to be introduced into the hybrid reactor for the first time;
a discharge system for discharging treated waste water from the hybrid reactor,
a central flow channel extending from the top of the hybrid reactor in downward direction from a first distance from the upper confines of the reactor to a second distance from the lower reactor;
the hybrid reactor being structured to allow the waste water flow in the hybrid reactor in a loop through the central flow channel in downward direction, then through the space in the lower portion, then along the carrier elements in upward direction, and finally again into the central flow channel;
a space between the central flow channel and a wall of the hybrid reactor in which the carrier elements are positioned, the space extending for at least part of the height of the flow channel, the carrier elements forming a structured, ordered fixed bed to permit flow therethrough, the carrier elements being arranged with flow passages having a predetermined width range between adjacent carrier elements; and
a separator system located in the upper portion of the hybrid reactor below the discharge system, the separator system being structured to retain microorganisms floating in the waste water in the hybrid reactor.

28. The hybrid reactor of claim 27 wherein the carrier elements comprise plate-shaped carrier elements.

29. The hybrid reactor of claim 27 wherein a plurality of packages of the carrier elements are distributed across the circumference of the hybrid reactor, with the plate-shaped carrier elements within each package being arranged parallel to each other and in tangential direction of the hybrid reactor.

30. The hybrid reactor of claim 27 wherein the flow passages between adjacent carrier elements each have a width of between 3 and 6 cm.

31. The hybrid reactor of claim 27 wherein the separator system comprises a partition provided in spaced apart manner above the upper end of the central flow channel and covering a major part of the reactor cross-sectional area while leaving free an outer annular area.

32. The hybrid reactor of claim 27, further comprising a first discharge line for gas formed in the hybrid reactor and structured to remove the gas in the upper portion of the hybrid reactor.

33. The hybrid reactor of claim 27 wherein the carrier plates are positioned in 15 to 40% of the reactor volume.

34. The hybrid reactor of claim 27, further comprising a flow hindrance positioned on the wall of the lower portion of the hybrid reactor.

35. The hybrid reactor of claim 27, further comprising at least one driving jet outlet terminating below the lower end of the central flow channel.

36. The hybrid reactor of claim 27, further comprising immobilized microorganisms and microorganism pellets, the microorganisms in the pellets being different from the immobilized microorganisms.

37. A hybrid reactor for anaerobic waste water treatment, comprising:
a plurality of porous carrier elements occupying at least part of the height of the hybrid reactor;
a space in a lower portion of the hybrid reactor between the lower confines thereof and the carrier elements;
an upper portion of the hybrid reactor between the upper confines thereof and the carrier elements;
a supply line for waste water to be treated and to be introduced into the hybrid reactor for the first time;
a discharge system for discharging treated waste water from the hybrid reactor,
a central flow channel extending from the top of the hybrid reactor in downward direction from a first distance from the upper confines of the reactor to a second distance from the lower reactor;
the hybrid reactor being structured to allow the waste water flow in the hybrid reactor in a loop through the central flow channel in downward direction, then through the space in the lower portion, then along the carrier elements in upward direction, and finally again into the central flow channel;
a space between the central flow channel and a wall of the hybrid reactor in which the carrier elements are positioned, the space extending for at least part of the height of the flow channel, the carrier elements forming a structured, ordered fixed bed to permit flow therethrough, the carrier elements being arranged with flow passages having a predetermined width range between adjacent carrier elements;
a separator system located in the upper portion of the hybrid reactor below the discharge system, the separator system being structured to retain microorganisms floating in the waste water in the hybrid reactor; and
a flow hindrance positioned on the wall of the lower portion of the hybrid reactor.

38. The hybrid reactor of claim 37 wherein the carrier elements comprise plate-shaped carrier elements.

39. The hybrid reactor of claim 37 wherein the flow passages between adjacent carrier elements each have a width of between 3 and 6 cm.

40. The hybrid reactor of claim 37 wherein the carrier elements comprise carrier elements substantially of plastics particles and expanded clay particles that are unified with each other.

41. The hybrid reactor of claim 37 wherein the withdrawal member comprises an intermediate space between two plate-like elements as well as a conduit starting in the intermediate space.

42. The hybrid reactor of claim 37 wherein the separator system comprises a partition provided in spaced apart manner above the upper end of the central flow channel and covering a major part of the reactor cross-sectional area while leaving free an outer annular area.

43. The hybrid reactor of claim 37, further comprising a first discharge line for gas formed in the hybrid reactor and structured to remove the gas in the upper portion of the hybrid reactor.

44. The hybrid reactor of claim 37 wherein the carrier plates are positioned in 15 to 40% of the reactor volume.

45. The hybrid reactor of claim 37 further comprising at least one driving jet outlet terminating below the lower end of the central flow channel.

46. The hybrid reactor of claim 37, further comprising immobilized microorganisms and microorganism pellets, the microorganisms in the pellets being different from the immobilized microorganisms.

47. A hybrid reactor for anaerobic waste water treatment, comprising:
a plurality of carrier elements occupying at least part of the height of the hybrid reactor;
a space in a lower portion of the hybrid reactor between the lower confines thereof and the carrier elements;
an upper portion of the hybrid reactor between the upper confines thereof and the carrier elements;
a supply line for waste water to be treated and to be introduced into the hybrid reactor for the first time;
a discharge system for discharging treated waste water from the hybrid reactor,
a central flow channel extending from the top of the hybrid reactor in downward direction from a first distance from the upper confines of the reactor to a second distance from the lower reactor;
the hybrid reactor being structured to allow the waste water flow in the hybrid reactor in a loop through the central flow channel in downward direction, then through the space in the lower portion, then along the carrier elements in upward direction, and finally again into the central flow channel;
a space between the central flow channel and a wall of the hybrid reactor in which the carrier elements are positioned, the space extending for at least part of the height of the flow channel, the carrier elements forming a structured, ordered fixed bed to permit flow therethrough, the carrier elements being arranged with flow passages having a predetermined width range between adjacent carrier elements;
a separator system located in the upper portion of the hybrid reactor below the discharge system, the separator system being structured to retain microorganisms floating in the waste water in the hybrid reactor; and
a plurality of different kinds of microorganisms in the form of immobilized microorganisms and microorganism pellets, the microorganisms in the pellets being different from the immobilized microorganisms.

48. The hybrid reactor of claim 47 wherein the carrier elements comprise plate-shaped carrier elements.

49. The hybrid reactor of claim 47 wherein the flow passages between adjacent carrier elements each have a width of between 3 and 6 cm.

50. The hybrid reactor of claim 47 wherein the carrier elements comprise carrier elements substantially of plastics particles and expanded clay particles that are unified with each other.

51. The hybrid reactor of claim 47 wherein the withdrawal member comprises an intermediate space between two plate-like elements as well as a conduit starting in the intermediate space.

52. The hybrid reactor of claim 47 wherein the separator system comprises a partition provided in spaced apart manner above the upper end of the central flow channel and covering a major part of the reactor cross-sectional area while leaving free an outer annular area.

53. The hybrid reactor of claim 47, further comprising a first discharge line for gas formed in the hybrid reactor and structured to remove the gas in the upper portion of the hybrid reactor.

54. The hybrid reactor of claim 47 wherein the carrier plates are positioned in 15 to 40% of the reactor volume.

55. The hybrid reactor of claim 47, further comprising a flow hindrance positioned on the wall of the lower portion of the hybrid reactor.

56. The hybrid reactor of claim 47, further comprising at least one driving jet outlet terminating below the lower end of the central flow channel.

57. A hybrid reactor for anaerobic waste water treatment, comprising:

a plurality of microorganism pellets;

a plurality of carrier elements occupying at least part of the height of the hybrid reactor for immobilizing microorganisms;

a space in a lower portion of the hybrid reactor between the lower confines thereof and the carrier elements to contain the plurality of microorganism pellets for degradation of waste water contamination by the microorganism pellets;

an upper portion of the hybrid reactor between the upper confines thereof and the carrier elements;

a supply line for waste water to be treated and to be introduced into the hybrid reactor;

a discharge system for discharging treated waste water from the hybrid reactor, a central flow channel extending from the top of the hybrid reactor in downward direction from a first distance from the upper confines of the reactor to a second distance from the lower confines of the reactor;

the hybrid reactor being structured to allow the waste water flow in the hybrid reactor in a loop through the central flow channel in downward direction, then through the space in the lower portion, then along the carrier elements in upward direction, and finally again into the central flow channel;

the carrier elements positioned in an annular space between the central flow channel and a wall of the hybrid reactor for at least part of the height of the flow channel for immobilizing microorganisms, the carrier elements comprising a structured, ordered fixed porous bed to permit flow therethrough, the carrier elements being arranged with flow passages having a predetermined width range between adjacent carrier elements;

a separator system located in the upper portion of the hybrid reactor below the discharge system to retain the microorganisms floating in the waste water in the hybrid reactor;

the waste water inclusive of the microorganism pellets flowing in the hybrid reactor in a loop through the central flow channel in downward direction, then through the space in the lower portion, then along the carrier elements in upward direction and finally again into the central flow channel; and a recirculation system structured to withdraw water from the second partial flow and recirculate the withdrawn water into the waste water loop flow, the recirculation system including a withdrawal member positioned above a portion of the separator system and at a lower level than the discharge system.

58. The hybrid reactor of claim 57 wherein the carrier elements comprise plate-shaped carrier elements.

59. The hybrid reactor of claim 57 wherein the flow passages between adjacent carrier elements each have a width of 3 to 6 cm.

60. The hybrid reactor of claim 57 wherein the carrier elements comprise carrier elements substantially of plastics particles and expanded clay particles that are unified with each other.

61. The hybrid reactor of claim 57 wherein the separator system comprises a partition provided in spaced apart manner above the upper end of the central flow channel and covering a major part of the reactor cross-sectional area while leaving free an outer annular area.

62. The hybrid reactor of claim 57, further comprising a first discharge line for gas formed in the hybrid reactor and structured to remove gas in the upper portion of the hybrid reactor.

63. The hybrid reactor of claim 57 wherein the carrier plates are positioned in 15 to 40% of the reactor volume.

64. The hybrid reactor of claim 57, further comprising a flow hindrance positioned on the wall of the lower portion of the hybrid reactor.

* * * * *